(12) United States Patent
Kassab

(10) Patent No.: US 10,499,924 B2
(45) Date of Patent: Dec. 10, 2019

(54) DEVICES, SYSTEMS, AND METHODS FOR INVERTING AND CLOSING THE LEFT ATRIAL APPENDAGE

(71) Applicant: CVDevices, LLC, San Diego, CA (US)

(72) Inventor: Ghassan S. Kassab, La Jolla, CA (US)

(73) Assignee: CVDevices, LLC, San Diego, CA (US)

( * ) Notice: Subject to any disclaimer, the term of this patent is extended or adjusted under 35 U.S.C. 154(b) by 532 days.

(21) Appl. No.: 14/699,881

(22) Filed: Apr. 29, 2015

(65) Prior Publication Data
US 2016/0022273 A1    Jan. 28, 2016

Related U.S. Application Data

(63) Continuation-in-part of application No. 14/338,031, filed on Jul. 22, 2014, now Pat. No. 9,717,488.

(51) Int. Cl.
*A61B 17/00* (2006.01)
*A61B 17/12* (2006.01)
(Continued)

(52) U.S. Cl.
CPC .... *A61B 17/12122* (2013.01); *A61B 17/0057* (2013.01); *A61B 17/12172* (2013.01); *A61B 17/12013* (2013.01); *A61B 2017/00336* (2013.01); *A61B 2017/00561* (2013.01); *A61B 2017/00566* (2013.01); *A61B 2017/00575* (2013.01); *A61B 2017/00592* (2013.01); *A61B 2017/00597* (2013.01); *A61B 2017/00623* (2013.01); *A61B 2017/00867* (2013.01); *A61B 2017/1121* (2013.01); *A61B 2017/306* (2013.01); *A61B 2090/037* (2016.02)

(58) Field of Classification Search
CPC ............. A61F 2/852; A61B 17/0057; A61B 17/12022; A61B 17/221; A61B 2017/00561; A61B 2017/00566; A61B 2017/00575; A61B 2017/00592; A61B 2017/00597; A61B 2017/00615; A61B 2017/00623; A61B 2017/00632; A61B 2017/2215; A61B 17/12009; A61B 17/32056; A61B 2017/12013; A61B 2017/12018; A61B 1/00089
See application file for complete search history.

(56) References Cited

U.S. PATENT DOCUMENTS 5,100,419 A * 3/1992 Ehlers ................ A61B 17/0057
                                                                    606/140
5,207,686 A * 5/1993 Dolgin ............. A61B 17/32056
                                                                    606/1
(Continued)

*Primary Examiner* — Ryan J. Severson
*Assistant Examiner* — Christian D Knauss
(74) *Attorney, Agent, or Firm* — Reichel Stohry Dean LLP; Mark C. Reichel; Natalie J. Dean

(57) ABSTRACT

Devices, systems, and methods are disclosed for inverting and closing a left atrial appendage. Certain methods include the steps of inverting a distal portion of a left atrial appendage and constraining the inverted portion using at least a snare device configured to be fit around the inverted portion of the left atrial appendage and closed, so that the inverted portion is securely circumscribed and closed. Devices and systems related to such methods are also described and include a catheter system comprising a vacuum tube and a snare slidably disposed within a catheter.

19 Claims, 17 Drawing Sheets

(51) Int. Cl.
*A61B 17/11* (2006.01)
*A61B 17/30* (2006.01)
*A61B 90/00* (2016.01)

(56) References Cited

U.S. PATENT DOCUMENTS

| | | | | |
|---|---|---|---|---|
| 5,242,459 | A | * | 9/1993 | Buelna .............. A61B 17/12013 606/139 |
| 5,259,366 | A | * | 11/1993 | Reydel ............... A61B 1/00135 383/203 |
| 6,068,603 | A | * | 5/2000 | Suzuki .................. A61B 10/04 600/564 |
| 2002/0022837 | A1 | * | 2/2002 | Mazzocchi .......... A61B 17/122 606/41 |
| 2005/0131401 | A1 | * | 6/2005 | Malecki ............. A61B 17/0057 606/27 |
| 2008/0262514 | A1 | * | 10/2008 | Gasche ............. A61B 1/00135 606/139 |
| 2014/0200398 | A1 | * | 7/2014 | Hawkins ............ A61B 17/0469 600/37 |
| 2015/0257782 | A1 | * | 9/2015 | Cohn ............... A61B 17/22032 606/159 |

* cited by examiner

DEVICES, SYSTEMS, AND METHODS FOR INVERTING AND CLOSING THE LEFT ATRIAL APPENDAGE

PRIORITY

The present application is related to, claims the priority benefit of, and is a U.S. continuation application of U.S. patent application Ser. No. 14/338,031, filed Jul. 22, 2014, which is co-pending as of the filing date of this application and is related to, and claims the priority benefit of, U.S. patent application Ser. No. 13/537,394, filed on Jun. 29, 2012 and issued as U.S. Pat. No. 8,784,469 on Jul. 22, 2014, which is related to, and claims the priority benefit of, U.S. Provisional Patent Application Ser. No. 61/503,428, filed Jun. 30, 2011. The contents of each of the aforementioned applications and patents are hereby expressly incorporated herein by reference in their entireties into this disclosure.

BACKGROUND

The present disclosure relates generally to medical devices and methods, such as those useful for inverting and closing a left atrial appendage.

Atrial fibrillation (AF) is the most common cardiac arrhythmia and affects millions of people worldwide, with the incidence expected to increase significantly in coming years. While AF is not a serious cardiac risk factor, it is very significant risk factor for stroke. AF produces a large number of arterial emboli that can enter cerebral circulation and cause stroke. AF is estimated to cause about 25% of all strokes and increases the risk of stroke in an individual by 500% when compared to people with normal sinus rhythm. Over 90% of such embolic strokes originate with clots released from the left atrial appendage (LAA), and a number of procedures and tools have been developed in an attempt to isolate the left atrial appendage and reduce the incidence of stroke, particularly in people suffering from AF.

The left atrial appendage is a windsock-like structure which extends from the left atrium and creates a side chamber which can be a site of increased clot formation and accumulation. There is some evidence that AF can further increase the tendency for clot to accumulate in the LAA, and the rapid contraction of the heart which accompanies AF can initiate the release of emboli and the consequent risk of stroke.

Both percutaneous and intravascular approaches have been proposed for LAA closure. Although some of these devices have now received regulatory approval, such systems are subject to a number of potential drawbacks. In particular, the present systems may be subject to incomplete LAA closure, dislodgement of the device, blood clot formation on the device, and the like. For these reasons, it would be desirable to provide improved LAA closure devices and protocols which produce at least some of these risks.

BRIEF SUMMARY

Exemplary embodiments of the present disclosure include systems for inverting and closing a left atrial appendage. In at least one exemplary embodiment, the system comprises a catheter configured for introduction into a mammalian blood vessel and advancement to a left atrium of a heart and into a left atrial appendage, a vacuum tube, and a snare, with the vacuum tube and snare being slidably disposed within the lumen of the tubular body and each configured for advancement through the distal end of the tubular body.

The catheter of the system comprises an elongated tubular body having a proximal end, a distal end, and defines a lumen extending between the proximal and distal ends. The vacuum tube comprises a proximal end, a distal end, and a first lumen extending between the proximal and distal ends. Furthermore, the distal end of vacuum tube is configured to engage a targeted tissue. For example, in at least one embodiment, the distal end of the vacuum tube comprises a suction flange.

In at least one embodiment, the catheter system further comprises a vacuum source coupled with the vacuum tube. Here, the vacuum source is operable to generate a vacuum within the first lumen of the vacuum tube to facilitate engagement of the target site using the distal end of the vacuum tube.

The snare of the catheter system comprises an elongated wire having a proximal end, a distal end, and a separation mechanism. The distal end of the snare is configured to move from an open position to a closed position. In at least one embodiment, the snare is configured to lock in the closed position once moved thereto. The separation mechanism of the snare configured to detach the distal end of the snare from the proximal end upon activation (the application of a proximal force, such as by pulling the proximal end thereof, for example).

In at least one embodiment, the separation mechanism comprises a slicing or cutting mechanism or a snap-fastener system. In at least one exemplary embodiment, the separation mechanism comprises a weakened region of the elongated wire.

The snare may be slidably disposed directly within the lumen of the tubular body adjacent to, and external of, the vacuum tube. Alternatively, the vacuum tube may further comprise a second lumen extending between the proximal and distal ends thereof and concentric with the first lumen, and the snare may be slidably disposed within the second lumen of the vacuum tube. In the latter embodiment, at least the distal end of the snare is configured for advancement through the distal end of the vacuum tube. Furthermore, where the vacuum tube comprises a second lumen and the snare is slidably disposed therein, the first lumen of the vacuum tube comprises a first diameter and the second lumen of the vacuum tube comprises a second diameter, with the second diameter being greater than the first diameter.

The open position of the distal end of the snare may be configured to receive a portion of the left atrial appendage after inversion thereof. Likewise, the closed position of the distal end of the snare may be configured to engage and retain at least a portion of the left atrial appendage after the inversion thereof.

In an additional embodiment of the catheter systems of the present disclosure, the system further comprises an outer scaffold and an occluder membrane. Perhaps more specifically, a system for inverting and occluding a left atrial appendage comprises at least a catheter, a vacuum tube, a snare, an outer scaffold, and an occluder membrane coupled with the outer scaffold. The catheter, vacuum tube, and snare are configured in accordance with the embodiments of the system previously described. The outer scaffold is coupled with an exterior of the tubular body. Furthermore, the outer scaffold is configured for expansion and to be anchored within an interior of the left atrial appendage upon expansion. The occluder membrane is coupled to the outer scaffold and configured to move from a constricted position to an expanded position. The expanded position of the occluder membrane is sized and shaped (i.e. configured) for occluding an orifice of the left atrial appendage.

Methods for closing a left atrial appendage are also provided. In at least one exemplary embodiment, a method for closing a left atrial appendage of the present disclosure comprises the steps of: inverting a distal portion of a left atrial appendage; and constraining the inverted distal portion of the left atrial appendage using a catheter system configured to fit within an interior of the left atrial appendage, with the catheter system comprising: a catheter configured for introduction into a mammalian blood vessel and advancement into the left atrial appendage, the catheter comprising an elongated tubular body having a proximal end, a distal end, and defining a lumen extending between the proximal and distal ends, a vacuum tube comprising a proximal end, a distal end, and a first lumen extending between the proximal and distal ends, the distal end of vacuum tube configured to engage the distal portion of the left atrial appendage, and a snare comprising an elongated wire having a proximal end, a distal end and a separation mechanism, the distal end configured to move from an open position to a closed position and the separation mechanism configured to detach the distal end from the proximal end upon activation, wherein the vacuum tube and the snare are slidably disposed within the lumen of the tubular body and each configured for advancement through the distal end of the tubular body. The method may additionally comprise the step of locking the distal end of the snare in the closed position.

In at least one embodiment, the step of constraining comprises: introducing the distal end of the snare in the open position into the interior of the left atrial appendage; advancing the distal end of the snare in the open position distally along the inverted distal portion of the left atrial appendage; and moving the distal end of the snare to the closed position to engage the inverted distal portion of the left atrial appendage. Additionally or alternatively, the step of constraining is performed to facilitate closure of an orifice defined by the left atrial appendage and to promote fibrosis.

In yet another embodiment, the method may additionally or alternatively comprise the step of activating the separation mechanism to detach the distal end of the snare from the proximal end of the snare. In at least one embodiment, the separation mechanism comprises a slicing mechanism, a cutting mechanism, a weakened region of the elongated wire, or a snap-fastener mechanism. Furthermore, the step of activating the separation mechanism may comprise applying a proximal force to the snare.

In still further embodiments of the method, the first lumen of the vacuum tube comprises a first diameter, the second lumen of the vacuum tube comprises a second diameter, and the second diameter is greater than the first diameter. The step of inverting a distal portion of a left atrial appendage may comprise the steps of: introducing the vacuum tube into the interior of the left atrial appendage; applying suction through the vacuum tube so that the distal end of the vacuum tube engages the distal portion of the left atrial appendage; and pulling the vacuum tube in a direction away from the distal portion of the left atrial appendage while applying suction to invert the distal portion of the left atrial appendage and reduce a diameter of the inverted distal portion of the left atrial appendage to less than the second diameter.

Furthermore, where the catheter system additionally comprises an outer scaffold coupled with an exterior of the tubular body and an occluder membrane coupled to the outer scaffold and configured to move from a constricted position to an expanded position for occluding an orifice of the left atrial appendage, the method may further comprise the steps of: introducing the outer scaffold into the interior of the left atrial appendage; expanding the outer scaffold within the interior of the left atrial appendage to anchor the outer scaffold and initiate the expansion of the occluder membrane coupled therewith; and occluding an orifice of the left atrial appendage with the expanded outer scaffold.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

Figure 1A:
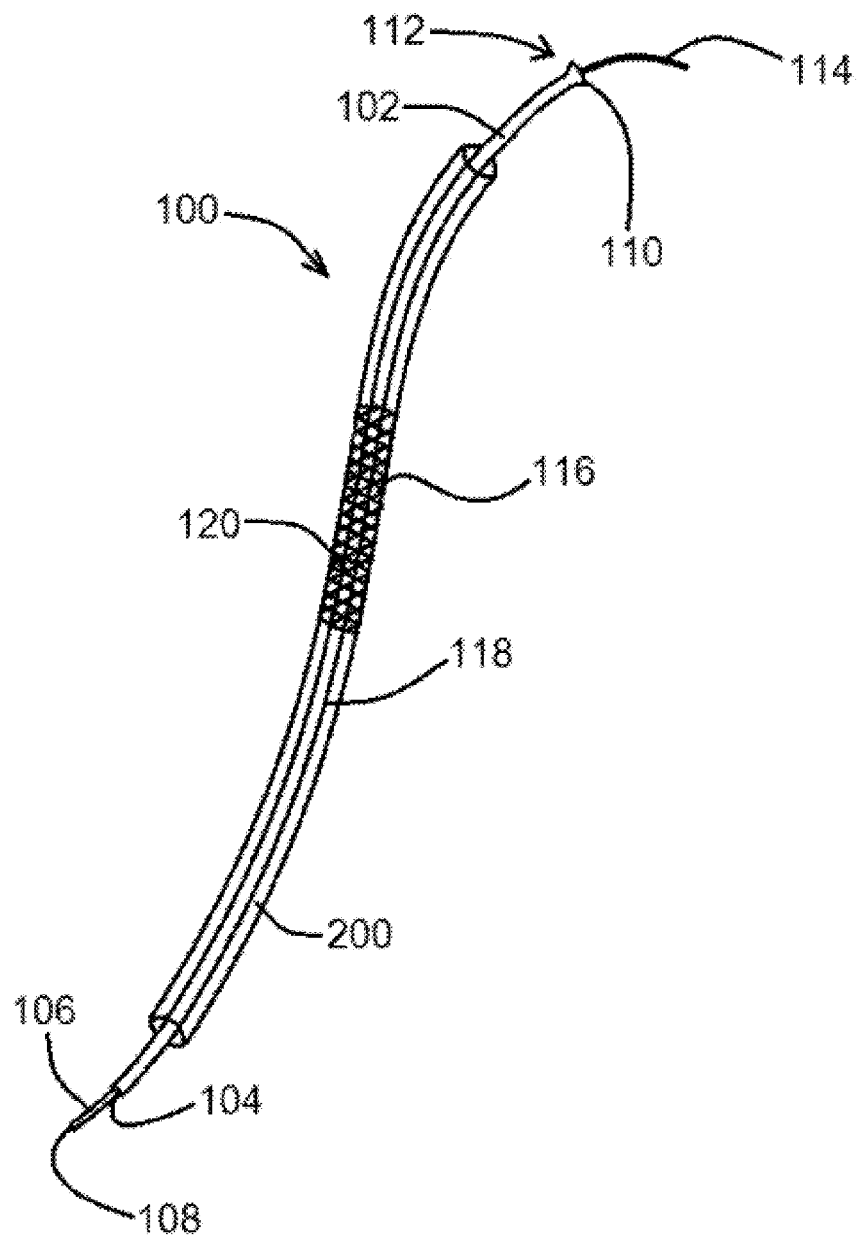
FIG. 1A shows portions of a catheter system useful to invert a left atrial appendage, according to an exemplary embodiment of the present disclosure.

An overview of the features, functions and/or configurations of the components depicted in the various figures will now be presented. It will be appreciated that not all of the features and components of the devices, systems and methods of the present disclosure are necessarily depicted in the figures. Likewise, it will be appreciated that not all of the features and components depicted in the figures are necessarily described. Some of these non-discussed features, such as various couplers, etc., as well as other discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended, with any additional alternations and modifications and further applications of the principles of this disclosure being contemplated hereby as would normally occur to one of skill in the art. On the contrary, this disclosure is intended to cover alternatives, modifications, and equivalents as may be included within the spirit and scope of this application as defined by the appended claims. While this technology may be illustrated and described in a preferred embodiment, the devices, systems, and methods hereof may comprise many different configurations, forms, materials, and accessories.

For example, the systems, methods and techniques of the present application will be described in the context of a catheter system for LAA closure. However, it should be noted that the devices, systems, methods, and techniques of the present application apply in a wide variety of contexts including, but not limited to, other tissue inversion applications.

In the following description, numerous specific details are set forth in order to provide a thorough understanding of the present disclosure. Particular examples may be implemented without some or all of these specific details. In other instances, well known operations and/or medical techniques have not been described in detail so as to not unnecessarily obscure the present disclosure.

In describing the various devices, systems, and mechanisms of the present disclosure, the description will sometimes describe a connection between two components. Words such as attached, affixed, coupled, connected, and similar terms with their inflectional morphemes are used interchangeably, unless the difference is noted or made otherwise clear from the context. These words and expressions do not necessarily signify direct connections, but include connections through mediate components and devices. It should be noted that a connection between two components does not necessarily mean a direct, unimpeded connection, as a variety of other components may reside between the two components of note. For example, a component of the catheter system of the present disclosure may be described as being slidably disposed within another component, but it will be appreciated that a variety of other tubes, materials, or other components may reside in between the two components of note. Likewise, while a vacuum source may be described herein as being coupled with a vacuum tube of the catheter system of the present disclosure, it will be appreciated that a variety of bridge devices or componentry may reside between the vacuum source and the vacuum tube. Consequently, a connection does not necessarily mean a direct, unimpeded connection unless otherwise noted.

The embodiments of the disclosure described herein are not intended to be exhaustive or to limit the invention to precise forms disclosed. Rather, the embodiments selected for description have been chosen to enable one skilled in the art to practice the disclosure. Furthermore, wherever feasible and convenient, like reference numerals are used in the figures and the description to refer to the same or like parts or steps. The drawings are in a simplified form and not to precise scale.

Figure 1B:
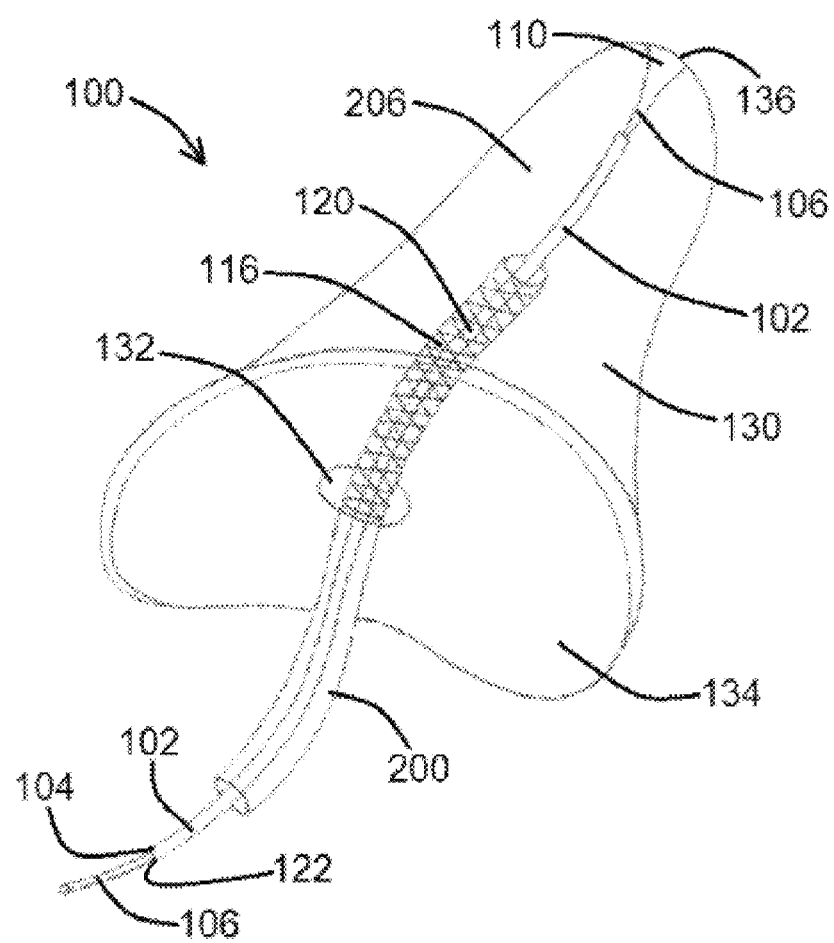
FIG. 1B shows portions of a catheter system positioned within a left atrial appendage, according to an exemplary embodiment of the present disclosure.

An exemplary catheter system for inverting closure of the left atrial appendage (LAA) of a heart of the present disclosure is shown in FIGS. 1A and 1B. As shown in FIG. 1A, an exemplary catheter system 100 constructed in accordance with the principles of the present disclosure comprises an elongated tubular body 102 defining a central passage or lumen 104 therethrough. A vacuum tube 106, in at least one embodiment, may be slidably disposed within the central lumen 104 of the tubular body 102, with vacuum tube 106 defining its own lumen 108 therethrough and having a suction flange 110 at the distal end 112 of vacuum tube 106. The vacuum tube 106 is connectible to a vacuum source 1100 (not shown in FIG. 1A, but shown in the general system figure in FIG. 11) so that vacuum (or negative pressure) can be applied through the lumen 108 of the vacuum tube 106 in order to allow the suction flange 110 to engage and adhere to the target site on the interior wall of the LAA, which may be at or near the apex of LAA. Vacuum tube 106, in at least one embodiment, may include a lumen for receiving a guidewire 114. A double stent assembly 116, as shown in FIG. 1A and referenced in further detail herein, can be carried on the exterior surface 118 of the tubular body 102 and delivered into the patient as described further herein.

As described in additional detail below, an exemplary double stent assembly 116 of the present disclosure includes an outer, self-expanding scaffold (stent) 202 which is maintained in a constrained or radially collapsed configuration by an outer sheath 200 configured to slidably engage tubular body 102 as shown in FIG. 1A. A balloon 120, coupled to tubular body 102, is configured to expand at least one of the stents of the double stent assembly 116 by way of inflation of balloon 120 using an inflation source 1102 (not shown in FIG. 1A, but shown in the general system figure in FIG. 11). Balloon 120 inflation, in at least one embodiment, may occur by way of inflation either through an inflation lumen 122 of tubular body 102 separate from central lumen 104, as shown in FIG. 1B for example, through central lumen 104, or through a separate inflation tube 124 (shown in FIG. 2A), so that a gas, a liquid, and/or another substance 126 can be delivered through one or more of inflation lumen 122, central lumen 104, and/or inflation tube 124, through an optional aperture 128 defined within tubular body 102 or balloon 120 itself, and into balloon 120. Deflation would be the opposite of inflation, whereby the gas, liquid, and/or substance 126 would exit balloon 120 through optional aperture 128.

Referring now to FIG. 1B, an exemplary catheter system 100 of the present disclosure may be deployed into the interior of the LAA 130 through the LAA orifice 132 within the left atrium wall 134. The suction flange 110 of the vacuum tube 106 may then engage the inner wall of the LAA 130, optionally within an apical region at or near the LAA apex 136, by way of suction from a vacuum source operably coupled to the vacuum tube.

Figure 2A:
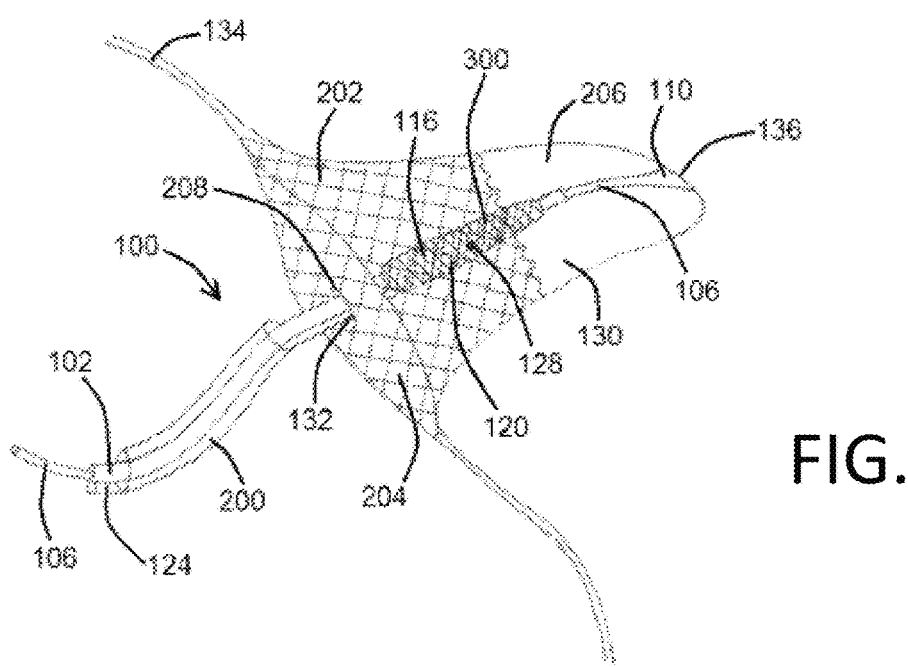
FIG. 2A shows portions of a catheter system positioned within a left atrial appendage with a deployed/expanded outer scaffold, according to an exemplary embodiment of the present disclosure.
Figure 2B:
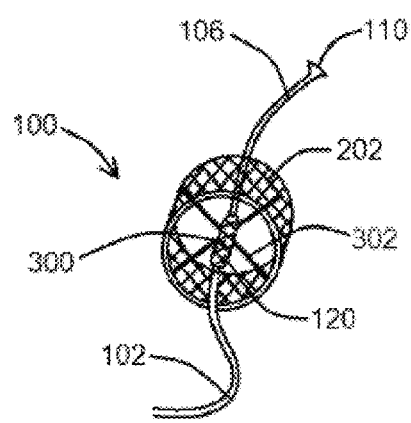
FIG. 2B shows portions of a catheter system with a deployed/expanded outer scaffold, according to an exemplary embodiment of the present disclosure.

Referring now to FIGS. 2A and 2B, after the tubular body 102 of the catheter system 100 has been properly positioned within the LAA 130, a sheath 200 surrounding at least part of tubular body 102 may be retracted away from the relative distal end of tubular body 102, allowing an outer scaffold 202 (which may be referred to herein as an "outer stent") of the double stent assembly 116 to expand and anchor within a region of the LAA 130 adjacent to the LAA orifice 132. The outer scaffold 202 carries and deploys an occluder membrane 204 across the LAA orifice 132 in order to inhibit or prevent emboli release during the closure process (such as during subsequent steps of exemplary methods/protocols as referenced herein) as well as, in at least one embodiment, permanently isolating the interior 206 of the LAA 130 after the methods/protocols has/have been completed. Occluder membrane 204, in various embodiments, may be composed of a variety of conventional and biocompatible materials capable of blocking the passage of emboli, including, but not limited to, various polytetrafluoroethylenes (PTFEs), polyurethanes, silicone rubbers, Dacron, and/or various biologic materials such as bovine pericardium, and the like.

Occluder membrane 204, in at least one embodiment, has a valve 208, which may be at or near the relative center of occluder membrane 204, which is configured to receive tubular body 102 and, as described in further detail below, allows the tubular body 102 to be removed at the end of the method/protocol. In at least one embodiment, valve 208 is self-closing so that after tubular body 102 has been removed, passage through valve 208 is fully closed and occluder membrane 204 is fully occlusive to the passage of emboli from the interior 206 of LAA 130. Suitable self-closing valves 208, by way of example, include but are not limited to flap valves, duck-billed valves, slit valves, and the like.

Figure 3A:
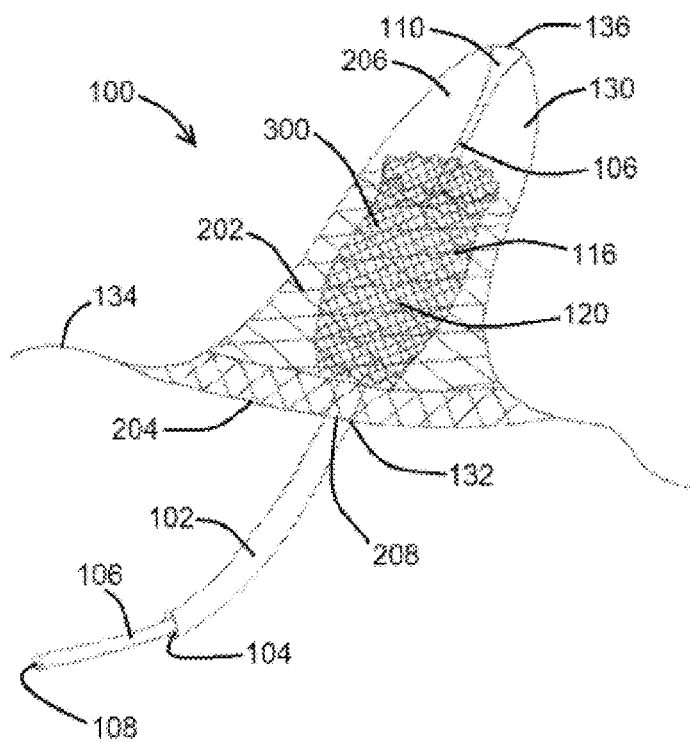
FIG. 3A shows portions of a catheter system positioned within a left atrial appendage with deployed/expanded outer and inner scaffolds, according to an exemplary embodiment of the present disclosure.
Figure 3B:
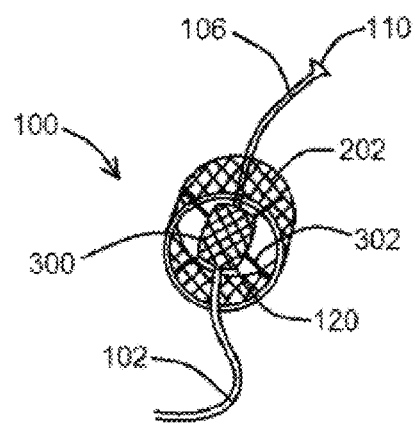
FIG. 3B shows portions of a catheter system with deployed/expanded outer and inner scaffolds, according to an exemplary embodiment of the present disclosure.

Referring now to FIGS. 3A and 3B, and either before or after occluder membrane 204 has been deployed, an inner scaffold 300 (which may be referred to herein as an "inner stent") is deployed, which may be by inflating balloon 120 on tubular body 102 which carries inner scaffold 300. A plurality of cables or tethers 302, in at least one embodiment, are provided between outer scaffold 202 and inner scaffold 300, as shown in FIG. 3B. Cables or tethers 302, in at least one embodiment, are configured to hold inner scaffold 300 in place after the tubular body 102 is removed.

Figure 4A:
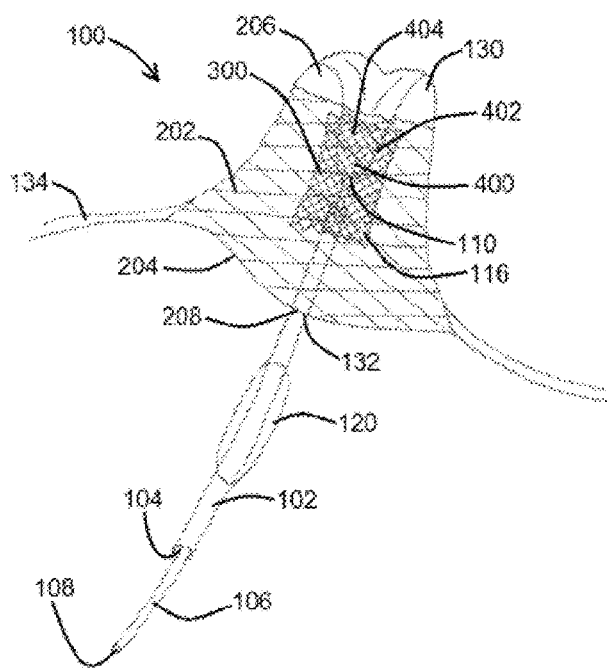
FIG. 4A shows portions of a catheter system positioned within a left atrial appendage with deployed/expanded outer and inner scaffolds and a portion of the left atrial appendage positioned within the inner scaffold, according to an exemplary embodiment of the present disclosure.
Figure 4B:
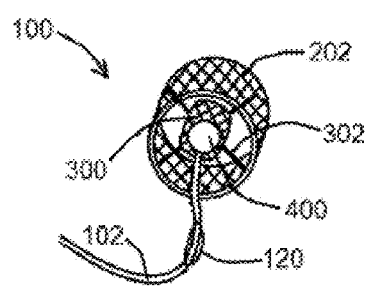
FIG. 4B shows portions of a catheter system with deployed/expanded outer and inner scaffolds and a portion of the left atrial appendage positioned within the inner scaffold, according to an exemplary embodiment of the present disclosure.

As shown in FIGS. 4A and 4B, after inner scaffold 300 has been expanded by balloon 120, balloon 120 may be deflated and tubular body 102 may be withdrawn from the patient. During or after withdrawal, vacuum or suction from vacuum source 1100 may be applied through vacuum tube 106 while suction flange 110 is reversibly affixed to LAA 130 in order to invaginate or invert a distal portion 400 of a wall 402 of the LAA 130. The inverted portion of wall 402, in at least one embodiment, may then be drawn into a central opening 404 defined within the expanded inner scaffold 300 while outer scaffold 202 maintains the position of the inner scaffold 300, using, for example, cables or tethers 302.

Figure 5:
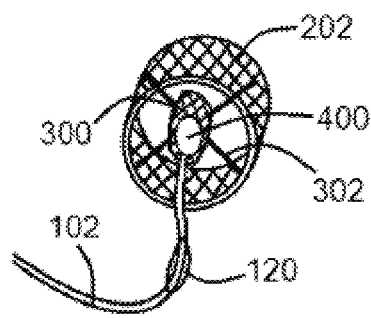
FIG. 5 shows an inner scaffold closed over the invagination or inverted portion of the left atrial appendage wall after the balloon has been deflated and withdrawn, according to an exemplary embodiment of the present disclosure.

Referring now to FIG. 5, after the distal portion 400 of LAA 130 has been drawn into the central opening 404 of inner scaffold 300, inner scaffold 300 will be allowed to close in over the distal portion 400 of LAA 130 in order to fully circumscribe and close that portion 400. Such inversion and circumferential closure will cause the tissue to fibrose over time, thus further reducing the risk of emboli formation and release from the occluded LAA 130. In at least one embodiment, inner scaffold 300 is self-closing. In at least another embodiment, A circumferentially constraining the inverted LAA comprises allowing a self-closing scaffold (such as inner scaffold 300) to collapse over the inverted LAA.

In at least one embodiment, and before or while the vacuum tube 106 is drawing the LAA 130 inwardly to invert LAA 130, the applied vacuum will also be drawing blood and other fluids from the interior 206 of LAA 130 to further encourage closure and allow for the volume reduction of the interior 206 of LAA 130 as it is being inverted.

Figure 6A:
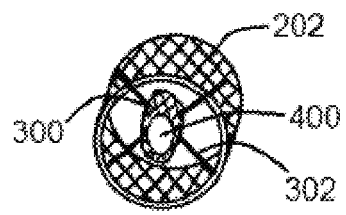
FIG. 6A shows an inner scaffold closed over the invagination or inverted portion of the left atrial appendage wall after the balloon catheter has been withdrawn, according to an exemplary embodiment of the present disclosure.
Figure 6B:
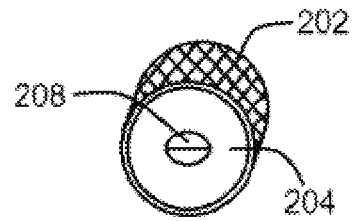
FIG. 6B shows an expanded outer scaffold with an occluder membrane covering one end and a valve positioned within the occluder membrane, according to an exemplary embodiment of the present disclosure.

After LAA 130 has been fully inverted, portions of catheter assembly 100 (such as tubular body 102 and vacuum tube 106) will be withdrawn through valve 208, leaving valve 208 closed and the occluder membrane 204 completely sealed off, as shown in FIGS. 6A and 6B. In a number of the previous figures, membrane 204 is not shown in order to provide an improved view of the interior of the double stent assembly 116. After membrane 204 has been deployed as referenced above, it remains in place (unless intentionally removed) in order to prevent emboli release during and after the implantation process. However, once tubular body 102 is withdrawn, valve 208 will close and the interior 206 of LAA 130 will be fully isolated from the left atrium.

In various embodiments of the present disclosure, it would be desirable to provide an exemplary catheter system 100 with an improved sealing mechanism about the periphery of the membrane to promote complete sealing of the interior of the LAA, particularly during the initial stages of the device deployment. As referenced herein, a "device" may comprise a double stent assembly of the present disclosure, and potentially additional components of an exemplary catheter system 100. For example, as shown on FIG. 7, portions of an exemplary catheter system 100 of the present disclosure comprise an occluder membrane 204 carried by a double stent assembly 116, disposed over a balloon 120, as generally described above/herein in connection with various other embodiments, and may include a sealing mechanism about its periphery in order to provide enhanced performance and sealing about the orifice 132 of the LAA 130.

Figure 7:
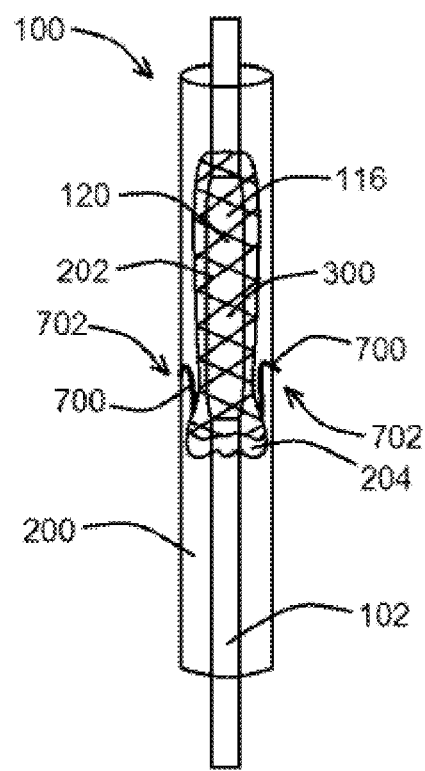
FIG. 7 shows portions of a catheter system useful to invert a left atrial appendage, according to an exemplary embodiment of the present disclosure.

As shown in FIG. 7, the enhanced seal may comprise one or more memory arms 700 (which may be an exemplary component of a memory flap 702, described in further detail herein), which are configured to capture and evert tissue about the LAA 130. Memory flap(s) 700 and occluder membrane 204 are initially constrained around the catheter (tubular body 102), typically by an external sheath 200 as shown in the figure. When sheath 200 is retracted to deploy the outer stent/scaffold 300 (as described in connection the previous embodiments), occluder membrane 204 and memory flap(s) 700 will deploy, as shown in FIG. 8.

Figure 8:
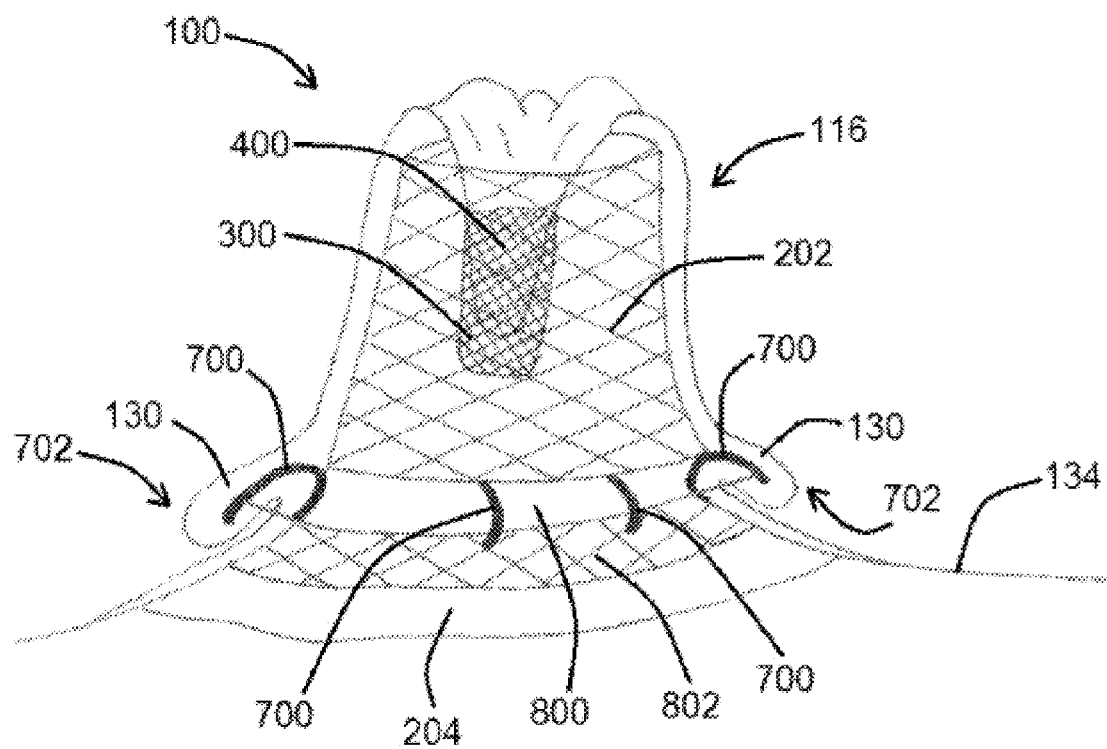
FIG. 8 shows a double stent assembly having memory arms and a flap membrane to seal against atrial wall or left atrial appendage tissue, according to an exemplary embodiment of the present disclosure.
Figure 9:
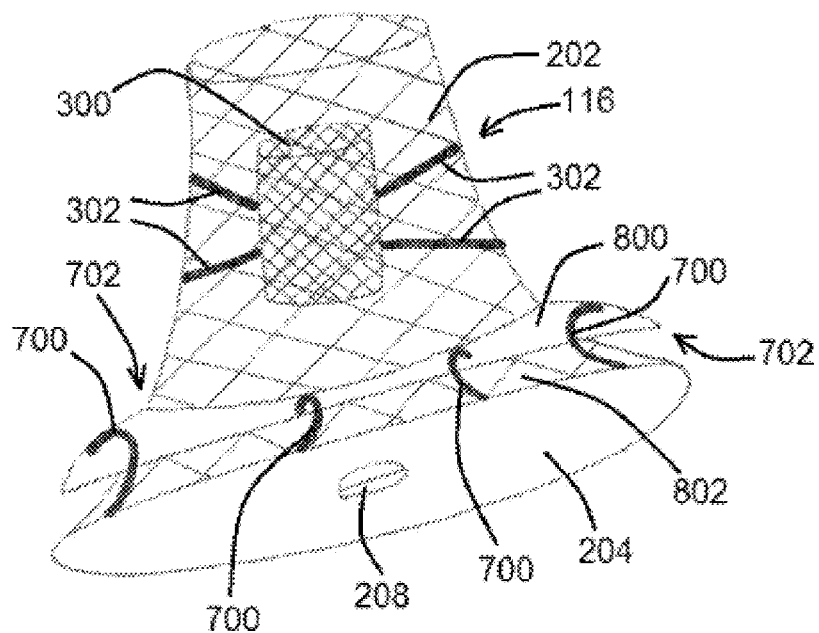
FIG. 9 shows a double stent assembly having memory arms and a flap, according to an exemplary embodiment of the present disclosure.

In at least one embodiment, and as shown in FIGS. 8 and 9, an exemplary memory flap 702 comprises a plurality of memory arms 700 and a flap membrane 800 mounted over memory arm(s) 700, wherein memory arms 700 can deploy outwardly to entrap LAA tissue 130 surrounding LAA orifice 132. In at least one embodiment, a flange portion of memory flap 702 extends from a lower portion of flap membrane 800 upwards and helps to position flap membrane 800 across LAA orifice 132 to provide the primary occlusion.

Figure 10:
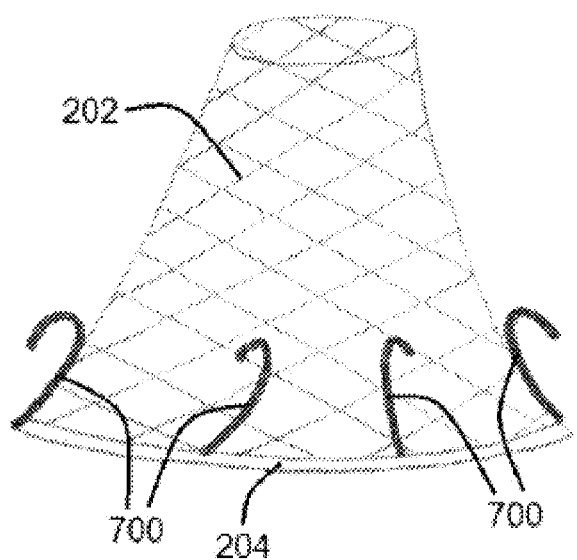
FIG. 10 shows an outer scaffold and an occluder membrane with memory arms extending therefrom, according to an exemplary embodiment of the present disclosure.

With reference the embodiments of portions of catheter systems 100 of the present disclosure shown in FIGS. 9 and 10, it can be seen that the memory arms 700 can be deployed downwardly in order to oppose the LAA 130 tissue and would typically form a part of a cylindrical external metallic self-expanding stent. Simple memory arm 700 material may include, but is not limited to, stainless steel, cobalt-chromium-nickel-molybdenum-iron alloys, tantalum, nitinol, nickel-titanium, polymer materials, and shape-memory polymers, such as polyurethanes, polytetrafluroethylenes, or other materials as described above.

Deployment of the double stent assemblies 116 as shown in FIGS. 7-9 (and the outer scaffold 202 shown in FIG. 10) may occur as referenced above in connection with other embodiments. However, in at least one embodiment, when flap membrane 800 is retracted, memory arm(s) 700 will deploy to place the flap membrane 800 downwardly to entrap the LAA 130 tissue in order to deploy the enhanced seal about occluder membrane 204. Such an embodiment has several advantages including the enhanced sealing as discussed above, an enhanced reinforcement or support of the occluder membrane 204, and for overall support for the deployed mechanism. Exemplary flap membrane 800 embodiments can also act as extension of the primary occluder membrane 204 to increase the LAA orifice 132 coverage.

Figure 11:
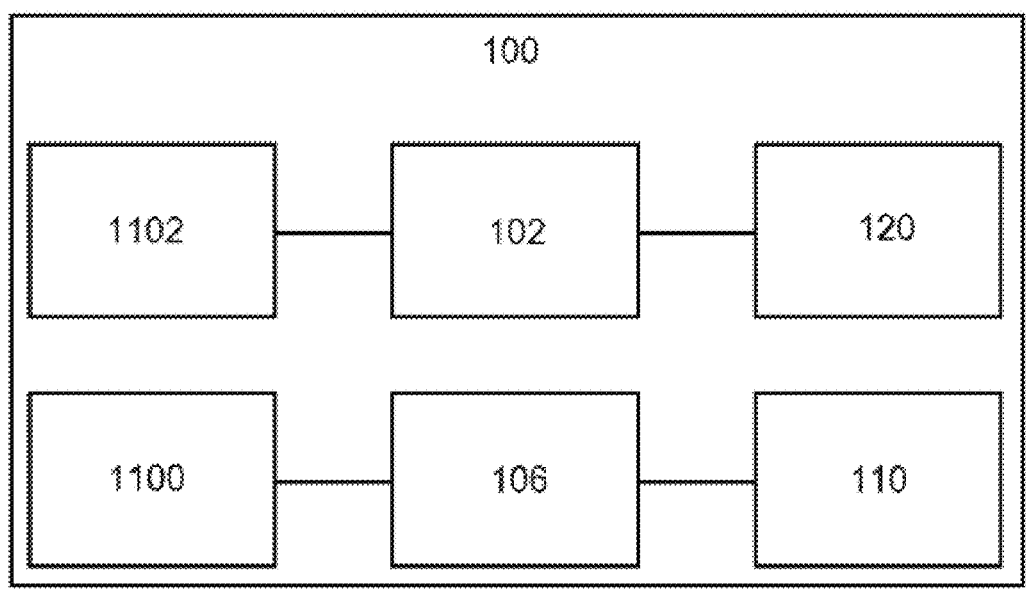
FIG. 11 shows a block diagram of components of a catheter system, according to an exemplary embodiment of the present disclosure.

FIG. 11 shows a block diagram of certain components of an exemplary catheter system 100 of the present disclosure. As shown therein, an exemplary catheter system 100 comprises an elongated tubular body 102 coupled to an inflation source 1102, with a balloon 120 coupled to the tubular body 102, so that inflation and deflation can occur using inflation source 1102. Further, an exemplary vacuum tube 106 is shown coupled to an exemplary vacuum source 1100, so that operation of vacuum source 1100 causes a vacuum within vacuum tube to facilitate engagement of a portion of a left atrial appendage 130 using suction flange 110. Additional components, as referenced herein, may comprise various embodiments of catheter systems 100.

Now referring to FIGS. 12A-13B, alternative embodiments of the catheter system 100 are shown. Similar to catheter system 100, exemplary catheter system 1200 of the present disclosure comprises an elongated tubular body 1202, a vacuum tube 1206, and a snare 1220. The tubular body 1202 is configured similarly to the tubular body 102 of catheter system 100. Perhaps more specifically, the tubular body 1202 at least defines a central passage or lumen 1204 therethrough and is configured for percutaneous or intravascular delivery. Similar to previously described embodiments, the tubular body 1202 may additionally include a lumen for receiving a guidewire (not shown) and an exterior surface 1218.

Figure 12A:
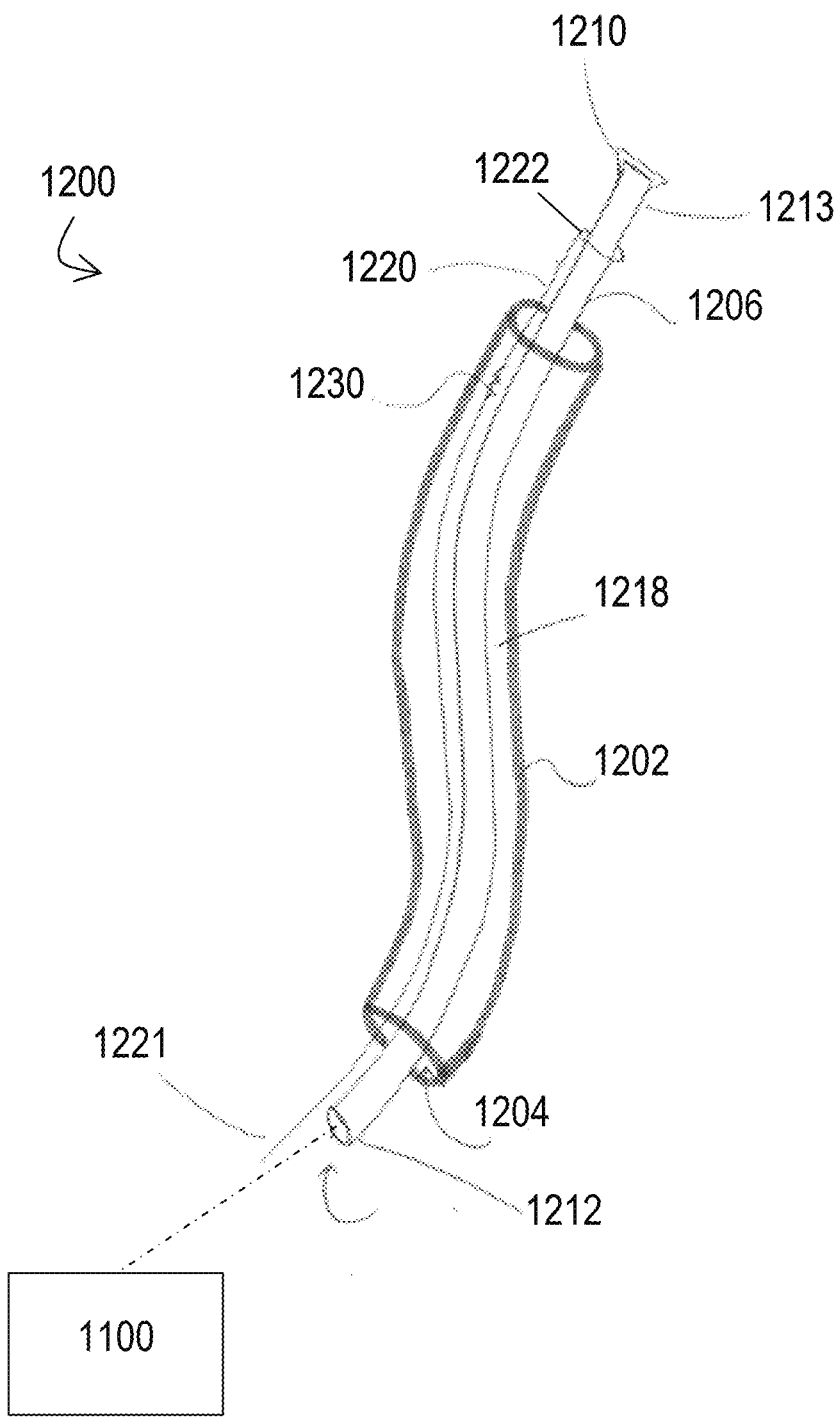
FIG. 12A shows portions of a catheter system useful to invert a left atrial appendage, according to at least one exemplary embodiment of the present disclosure.
Figure 12B:
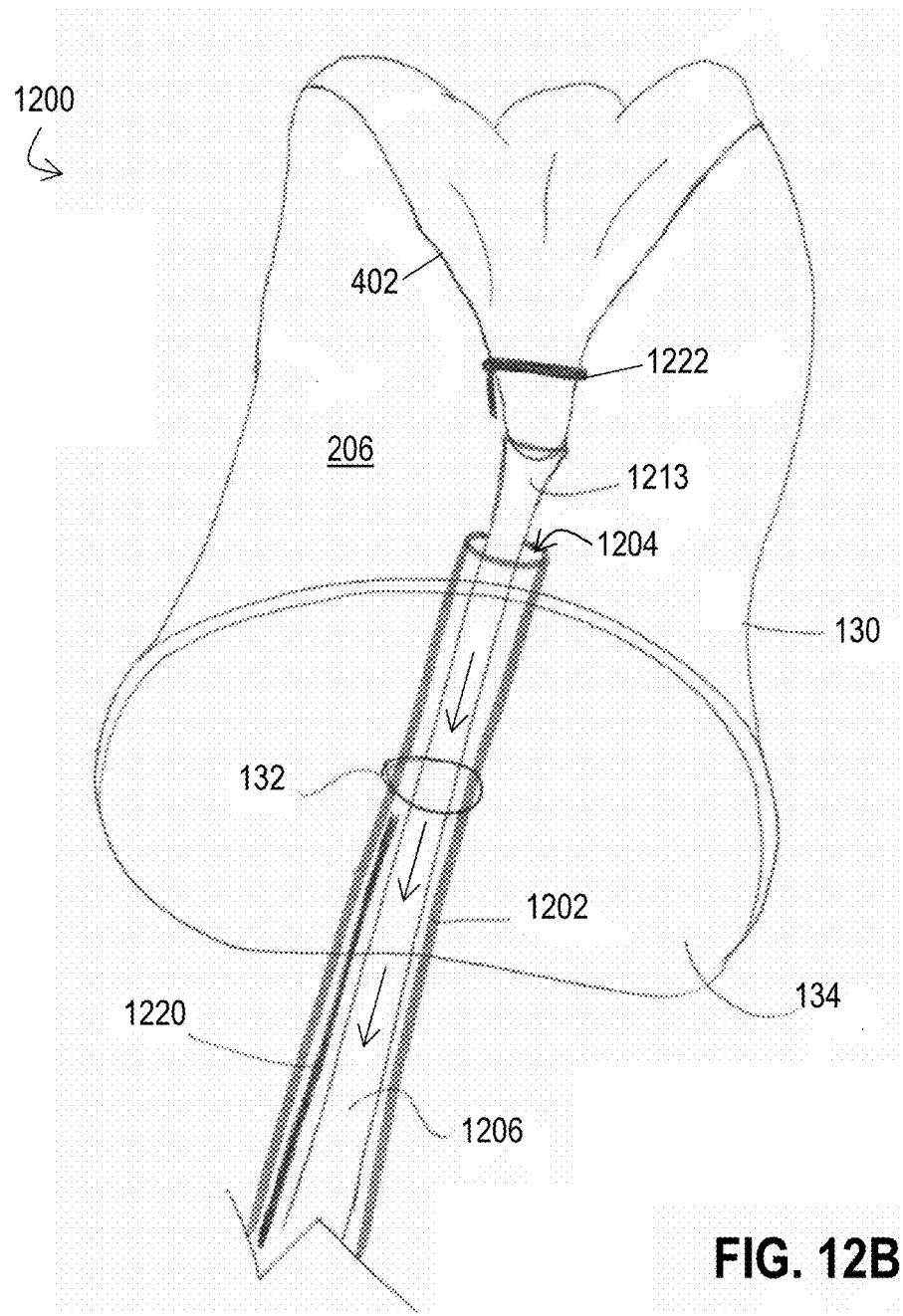
FIG. 12B shows portions of the catheter system shown in FIG. 12A positioned within a left atrial appendage with a deployed vacuum tube and detached distal end of a snare, according to an exemplary embodiment of the present disclosure.

In at least one embodiment, the vacuum tube 1206 is slidably disposed within the central lumen 1204 of the tubular body 1202 and defines its own lumen 1208 extending between a proximal end 1212 and a distal end 1213. The distal end 1213 of the vacuum tube 1206 is configured to be slidably advanced through the distal end of the tubular body 1202 and to engage tissue or a surface. For example, the distal end 1213 may be substantially cylindrical or, as shown in FIG. 12A, may comprise a suction flange 1210 having a conical-like shape. Furthermore, at least a portion of the distal end 1213 is open to the lumen 1208 so that a force can be emitted therethrough. The proximal end 1212 of the vacuum tube 1206 is connectible to a vacuum source 1100 such that suction (or negative pressure) can be transferred through the lumen 1208 of the vacuum tube 1206 and applied through the distal end 1213 thereof. Accordingly, when the vacuum source 1100 is operated and suction is applied to the proximal end 1212 of the vacuum tube 1206, a vacuum is created within the lumen 1208 and a suctional force is applied through the distal end 1213 of the vacuum tube 1206. In this manner, the distal end 1213 of the vacuum tube 1206 can be used to engage and adhere to a target site (e.g., on an interior wall 402 of the LAA 130) and even draw such tissue into the lumen 1208.

As previously noted, catheter system 1200 further comprises a snare 1220 slidably disposed within the lumen 1204 of the tubular body 1202 adjacent to the vacuum tube 1206. The snare 1220 is an elongated wire-like structure extending between a proximal end 1221 and a distal end 1222. The distal end 1222 of the snare 1220 is configured to move between an open and a closed configuration, for example when a force is applied to the proximal end 1221 (see the directional arrows in FIG. 12B). When in its open configuration, the distal end 1222 of the snare 1220 comprises a diameter that is sufficient to enable the distal end 1222 to be slidably positioned over the vacuum tube 1206 as shown in FIG. 12A and advanced around a target site. In the closed configuration however, the distal end 1222 is constricted such that anything positioned therein (e.g., the target site) is engaged thereby (see FIG. 12B). Accordingly, the distal end 1222 is capable of securely holding tissue when in the closed configuration. Furthermore, in at least one embodiment, the snare 1220 may lock after it is moved to the closed configuration. For example, after the snare 1220 is positioned around the target site, it may be moved to and locked in the closed configuration to securely and permanently engage and hold the tissue therein. Accordingly, the distal end 1222 of the snare 1220 may be used to secure an inverted LAA permanently (or for an extended period of time) after the other components of the catheter system 1200 are removed from the patient.

In at least one exemplary embodiment, the distal end 1222 of the snare 1220 comprises a lasso-like configuration that tightens (i.e. moves to the closed configuration) when the proximal end 1221 is pulled. It will be appreciated that other shapes and/or configurations of the distal end 1222 may be employed, provided the distal end 1222 is capable of advancing substantially over or around the target site when in the open configuration and tightening or clamping thereon when moved to the closed configuration.

The snare 1220 is composed of material(s) that allow for the snare 1220 to be percutaneously or intravascularly delivered within the lumen 1204 of the tubular body 1202 to the LAA. Accordingly, the wire-like structure of the snare 1220 may be flexible or semi-flexible, provided it also comprises enough rigidity that, in operation, the distal end 1222 can be advanced past the distal end 1213 of the vacuum tube 1206 and positioned around a target site.

In at least one exemplary embodiment, the snare 1220 further comprises a separation mechanism 1230 for electively detaching the distal end 1222 of the snare 1220 from its proximal end 1221. For example, as shown in FIG. 12A, the separation mechanism 1230 may be a weakened region of the wire-like structure that can be pulled to failure (represented in FIG. 12A by a zigzag). Additionally or alternatively, the separation mechanism 1230 may comprise a slicing or cutting mechanism, a snap-fastener configuration, or any other configuration capable of detaching the distal end 1222 from the remainder of the snare 1220 when activated by a user (via the application of a proximal force or otherwise).

Figure 13A:
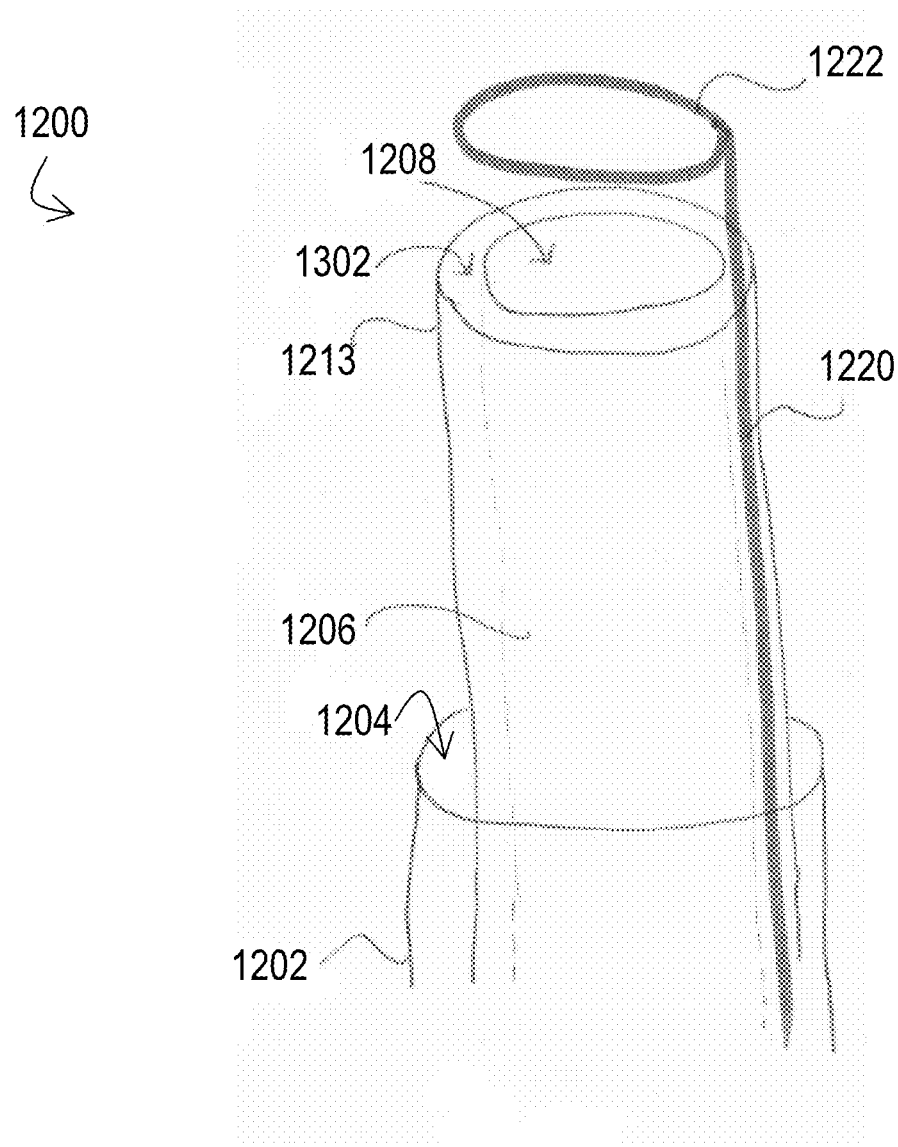
FIGS. 13A-13C show various views of portions of a catheter system comprising a snare positioned within a vacuum tube according to an exemplary embodiment of the present disclosure.
Figure 13B:
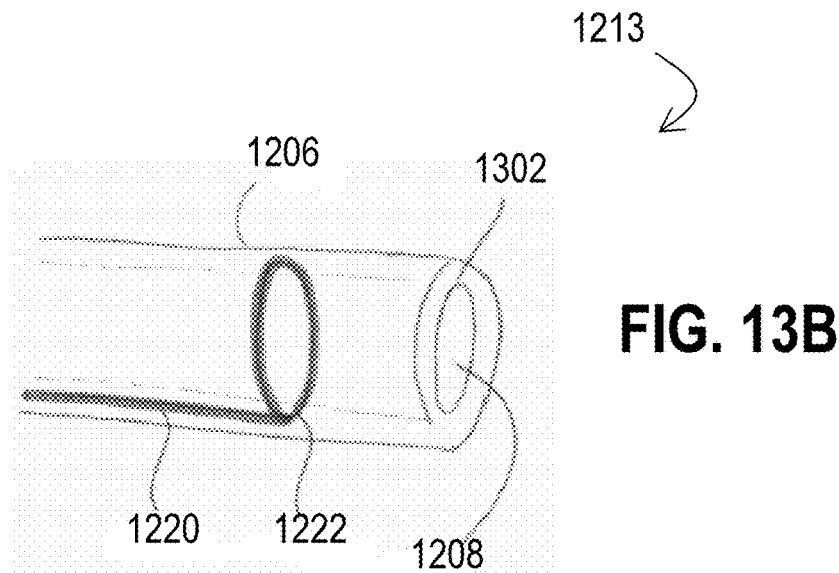
Figure 13C:
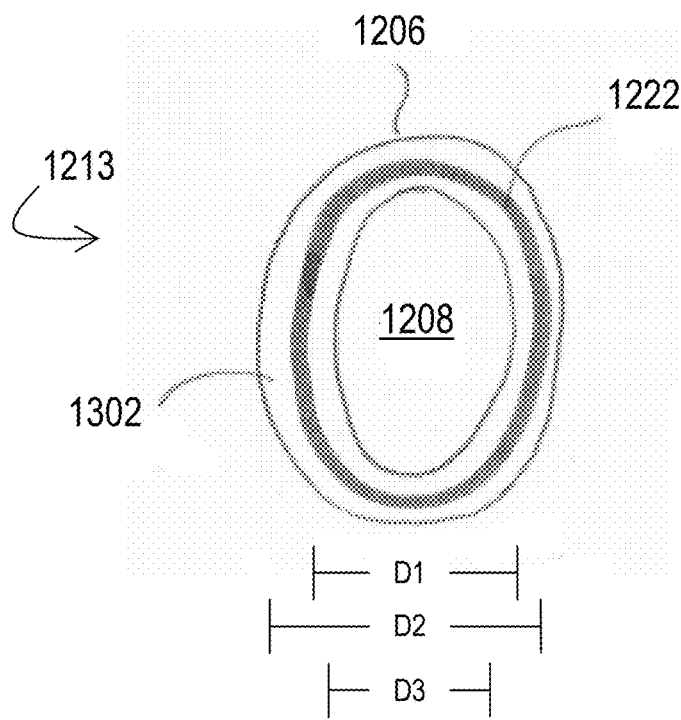

Now referring to FIGS. 13A-13C, an alternative embodiment of the catheter system 1200 is shown. Here, instead of the snare 1220 positioned within the lumen 1204 of the tubular body 1202 adjacent to the vacuum tube 1206, the snare 1220 is slidably positioned within the vacuum tube 1206. Perhaps more specifically, the vacuum tube 1206 further comprises a secondary lumen 1302 configured so the snare 1220 may be slidably advanced therethrough. As shown in FIG. 13C, the secondary lumen 1302 may be concentrically formed around the primary lumen 1208 of the vacuum tube 1206; however, it will be appreciated by one of skill in the art that the secondary lumen 1302 may comprise any configuration capable of receiving the snare 1220 and enabling its advancement through the distal end 1213 of the vacuum tube 1206.

Notably, in the embodiment where the snare 1220 is slidably disposed within the vacuum tube 1206, the diameter D1 of the distal end 1222 of the snare 1220 is less than the overall diameter D2 of the vacuum tube 1206, yet larger than the diameter D3 of the primary lumen 1208 (where suction is provided) (see FIG. 13C). This is significant in application because when the lumen 1204 is used to apply suction to a target site, the distal end 1222 of the snare 1220 will be larger than the diameter of any tissue drawn into the lumen 1208 and, thus, capable being positioned around the same. In this manner, the system 1200 can be used to deliver the snare 1220 to inverted LAA tissue such that the snare 1220 can fully circumscribe and close the inverted LAA.

As described herein, the embodiments of the catheter system 1200 of FIGS. 12A-13C do not require the inclusion of a balloon 120, the double stent assembly 116, the sheath 200, the memory arms 700, the flap membrane 800, nor the other components described in connection with the various embodiments of catheter system 100. However, if desired, one or more of the foregoing components may be incorporated into the catheter system 1200. For example, perhaps it is desired for the catheter system 1200 to include the outer scaffold 202 and occluder membrane 204 to inhibit or prevent emboli release during the closure process (such as during subsequent steps of the methods/protocols described herein) and/or to permanently isolate the interior 206 of the LAA 130 after the methods/protocols have been completed. Accordingly, the outer scaffold 202 may be positioned on the exterior surface 1218 of the tubular body 1202 and maintained in a constrained or radially collapsed configuration by the outer sheath 200, which is configured to slidably engage tubular body 1202, as shown in connection with the embodiments of FIGS. 1A-2A and 7. It will be understood that the only components of the catheter system 100 that are not straightforward to incorporate into the catheter system 1200 are the inner scaffold 300 of the double stent assembly 116 and the plurality of cables or tethers 302 attached thereto. Instead, in catheter system 1200, the inner scaffold 300 and the cables/tethers 302 are replaced with the snare 1220, which functions to close over and secure an inverted portion of the LAA 130.

Operation and delivery of the catheter system 1200 will now be described in connection with FIGS. 14A-14E and the method flow chart of FIG. 15. While such figures of FIGS. 14A-14E illustrate an embodiment of the system 1200 that comprises the snare 1220 slidably disposed within the secondary lumen 1302 of the vacuum tube 1206, such depiction is not intended to be limiting and it will be understood that method 1500 described herein may be used to deliver and operate alternative embodiments of the system 1200 in a similar fashion. Furthermore, FIGS. 14A-14E and method 1500 only illustrate and address the distal portion of the system 1200 (i.e. the distal ends 1213, 1222 of the vacuum tube 1206 and snare 1220, respectively). This limited perspective is used to provide an improved view of the relevant system 1200 components in order to promote understanding of the methodologies described herein and is not intended to be limiting. Indeed, where the system 1200 includes any additional components (such as the outer scaffold 202, occluder membrane 204, memory arms 700, flap membrane 800, etc.), such components may be operated and delivered with the catheter system 1200 as previously described in connection with catheter system 100.

Figures 14A, 14B:
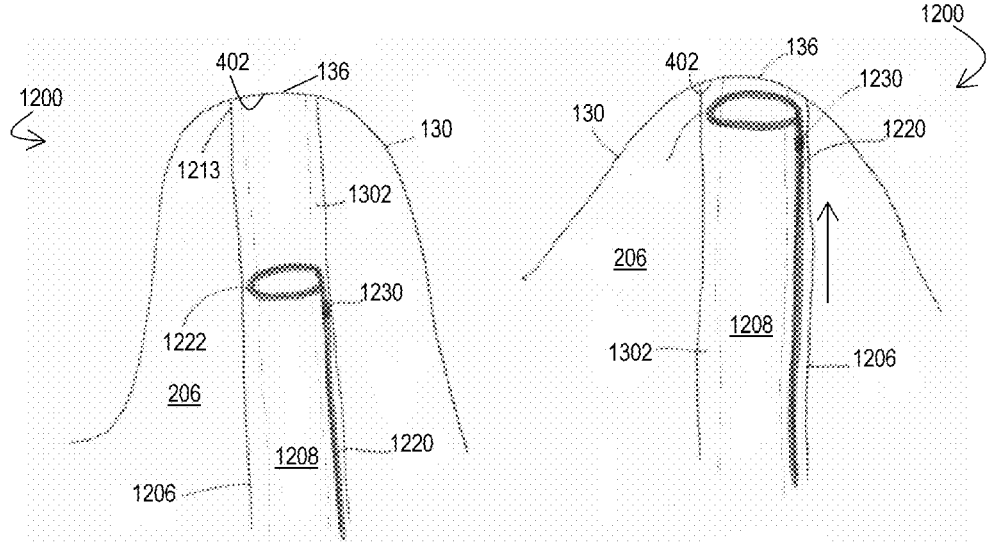
FIGS. 14A-14E show portions of a catheter system positioned within a left atrial appendage at various stages of deployment according to at least one exemplary embodiment of a method for inverting a left atrial appendage of the present disclosure.
Figure 15:
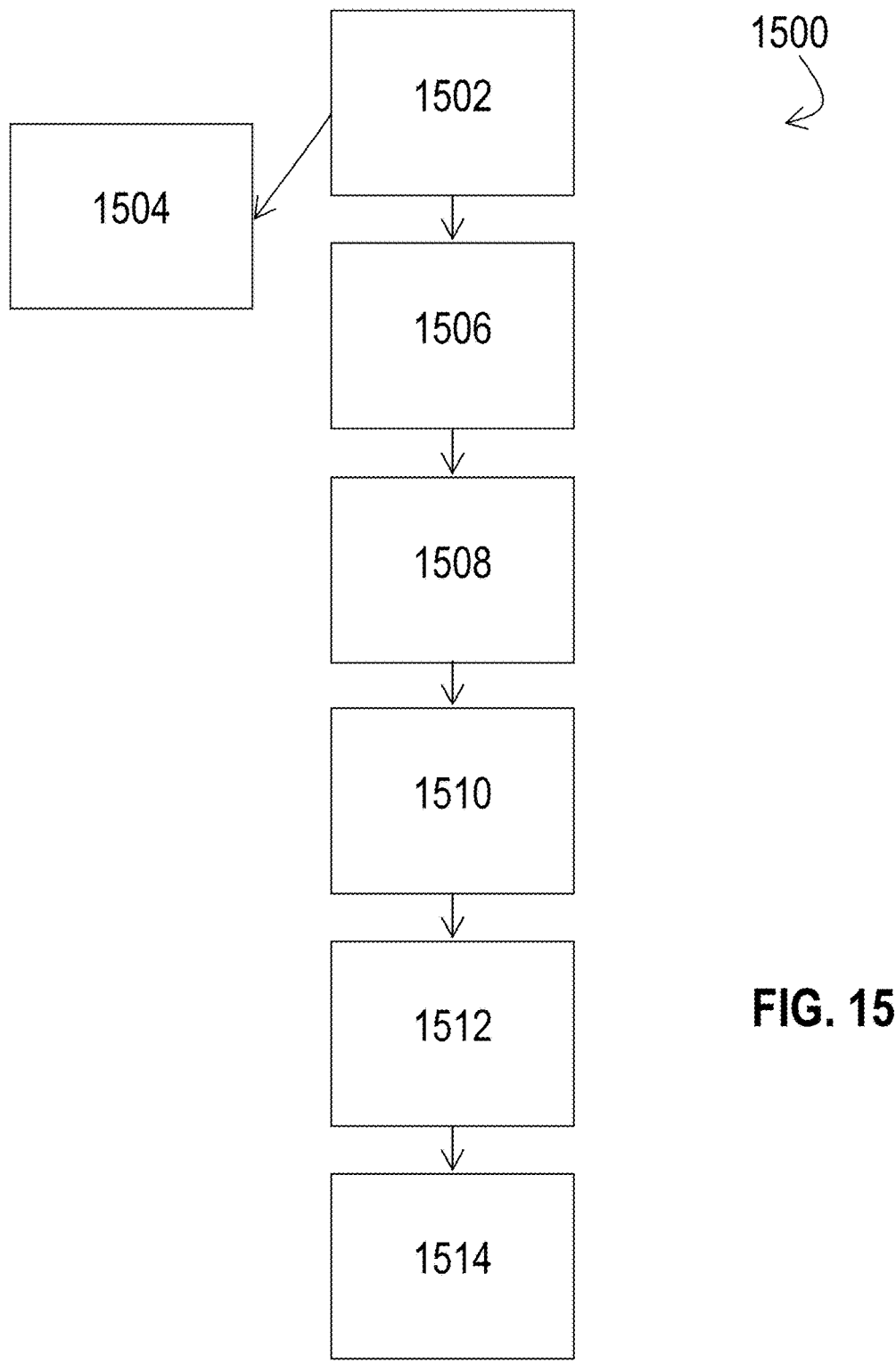
FIG. 15 shows a flow chart representative of a method for inverting and closing a left atrial appendage pursuant to an exemplary embodiment of the present disclosure.

Now referring to FIG. 14A, an exemplary embodiment of the catheter system 1200 of the present disclosure is deployed into the interior 206 of the LAA 130 through the LAA orifice 132 (not shown) within the left atrium wall 134 (not shown). At step 1502, the distal end 1213 of the vacuum tube 1206 is moved to engage the inner wall 402 of the LAA 130, optionally within an apical region at or near the LAA apex 136. At this step 1502, the snare 1220 is enclosed within the secondary lumen 1302 of the vacuum tube 1206 (or within the lumen 1204 of the tubular body 1202 and adjacent to the exterior of the vacuum tube 1206, as appropriate).

As shown in FIG. 14B, after the vacuum tube 1206 of the catheter system 1200 has been properly positioned relative to the target site (here, the LAA apex 136) within the LAA 130, the distal end 1222 of the snare 1220 may be advanced through the secondary lumen 1302 and toward the target site or wall 402 of the LAA 130 at optional step 1504. Notably, this snare 1220 advancement step 1504 may occur simultaneously with engaging the distal end 1213 of the vacuum tube 1206 with the target site/wall 402 (provided the snare 1220 is not advanced past the distal end 1213 of the vacuum tube 1206 at this step) or subsequent thereto.

Note that, in those embodiments where the snare 1220 is slidably disposed within the lumen 1204 of the tubular body 1202 (external of the vacuum tube 1206), the distal end 1222 of the snare 1220 may be advanced out of the tubular body 1202 at this step 1504 in conjunction with the vacuum tube 1206 or separately such that the snare 1220 is retained within the lumen 1204 of the tubular body 1204 until needed. Another delivery option includes advancing both the vacuum tube 1206 and the snare 1220 out of the tubular body 1202 at different rates such that the snare 1220 remains positioned around the vacuum tube 1206, but at a location between the distal end 1213 thereof and the distal end of the tubular body 1202.

Figures 14C, 14D:
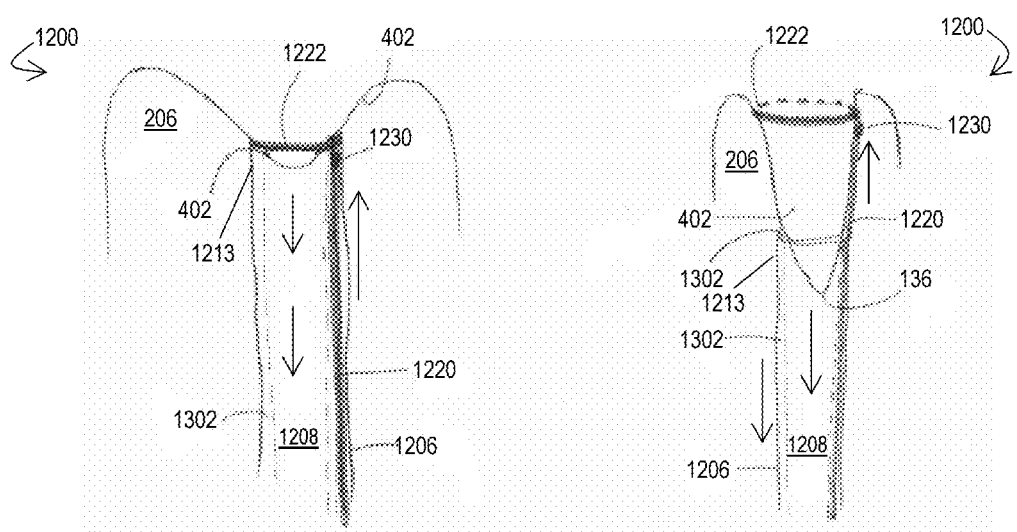

Referring now to FIGS. 14C and 14D, after the distal end 1213 of the vacuum tube 1206 has engaged the wall 402 of the LAA 130 (step 1502), at step 1506 vacuum or suction from vacuum source 1100 is applied from a vacuum source 1100 (not shown) operably coupled to the vacuum tube 1206 in order to reversibly affix the distal end 1213 to the wall 402 and invaginate or invert a distal portion 400 of a wall 402 of the LAA 130 by way of suction (suctional force denoted by direction arrows in the lumen 1208 of the vacuum tube 1206 in FIG. 14A). Accordingly, the engaged portion of the wall 402 is inverted and drawn (at least partially) into the lumen 1208 of the vacuum tube 1206. Additionally, while suction is at least maintained, the vacuum tube 1206 itself may be pulled in a proximal direction to further facilitate the inversion of the wall 402 (see the directional arrow of FIG. 14D adjacent to the vacuum tube 1206) at this step 1506. At step 1508, the distal end 1222 of the snare 1220 is advanced past the distal end 1213 of the vacuum tube 1206 and over the inverted wall 402 of the LAA 130. Steps 1506 and 1508 may be performed simultaneously, in sequence, or in alternating increments, as desired.

After the distal portion 400 of the LAA 130 is inverted to the desired degree at step 1506 and the snare 1220 is advanced at step 1508, the distal end 1222 of the snare 1220 is advanced distally over the inverted wall 402 and positioned at a desired location at step 1510 (see the directional arrow of FIG. 14D adjacent to the distal end 1222 of the snare 1220). Note that suction is maintained through the vacuum tube 1206 at this step 1510.

Once properly positioned, the snare 1220 is moved to the closed position and locked at step 1512 such that the inverted wall 402 surrounded thereby is engaged and securely constricted. For example, in the embodiment shown in FIGS. 14A-14E, the snare 1220 is moved to the closed configuration when the proximal end 1221 is pulled. In effect, closure of the snare 1220 fully circumscribes and closes the distal portion 400 of the LAA 130 and, thus, maintains the wall 402 in an inverted position.

Figure 14E:
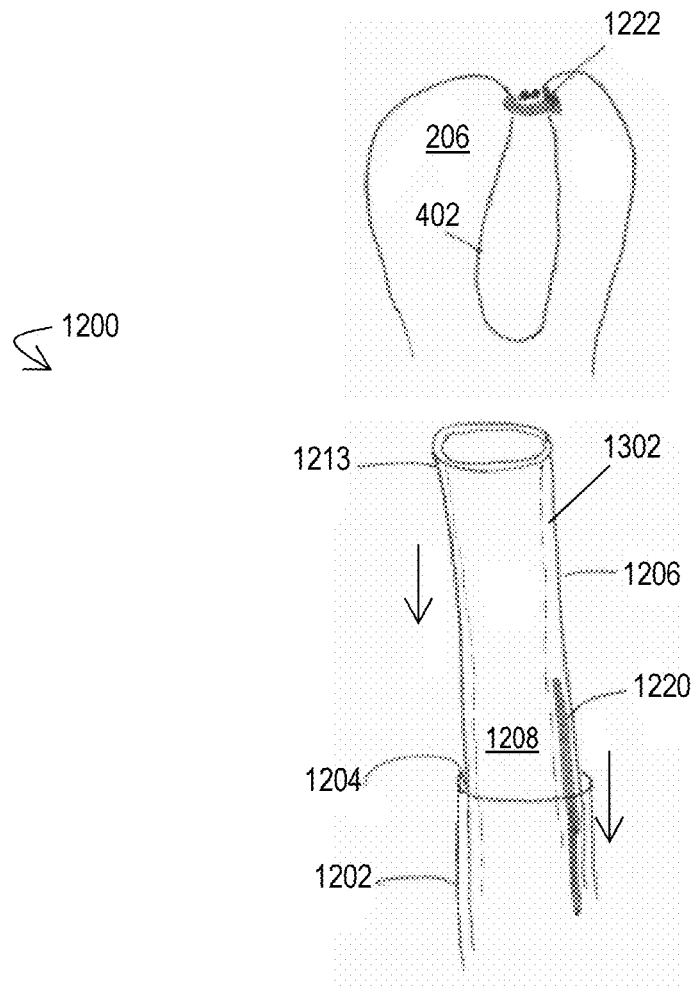

Now referring to FIG. 14E, after the LAA 130 has been inverted and secured by the snare 1220, at step 1514 the separation mechanism 1230 of the snare 1220 is implemented to detach the distal end 1222 from its proximal end 1221 such that portions of the catheter system 1200 may be withdrawn from the body. Where the separation mechanism 1230 comprises a weakened region, a sharp tug on the proximal end 1221 may be sufficient to achieve the desired detachment (see the directional arrow of FIG. 14E). Thereafter, portions of the catheter system 1200 (such as tubular body 1202, the vacuum tube 1206, and the remainder of the snare 1220) are withdrawn, leaving the distal end 1222 of the snare 1220 securely positioned around the inverted wall 402 of the LAA 130 for chronic placement or for a time period as otherwise desired. Alternatively, if desired, only the remainder of the snare 1220 may be withdrawn and a second (whole) snare 1220 may be loaded into the tubular body 1202 and/or vacuum tube 1206 for delivery to the left atrial appendage either to additionally secure the inverted LAA 130 or for other applications. After the procedure is complete, all portions of the catheter system 1200 other than the deployed distal end(s) 1222 of the snare 1220 are withdrawn.

While various embodiments of systems and devices for inverting and closing a left atrial appendage and methods of using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A system for inverting and closing a left atrial appendage, the system comprising:
a catheter configured for introduction into a mammalian blood vessel and advancement to a left atrium of a heart and into a left atrial appendage, the catheter comprising an elongated tubular body having a proximal end, a distal end, and defining a lumen extending between the proximal and distal ends;
a vacuum tube comprising a proximal end, a distal end, a first lumen, and a second lumen extending between the proximal and distal ends, the distal end of vacuum tube configured to engage a targeted tissue; and
a snare comprising an elongated wire having a proximal end, a distal end and a separation mechanism, the snare disposed within the second lumen of the vacuum tube and outside of the first lumen of the vacuum tube, the distal end configured to move from an open position to a closed position, and the separation mechanism integral with the proximal end of the elongated wire and configured to detach the distal end from the proximal end upon activation; and
wherein the vacuum tube and the snare are slidably disposed within the lumen of the elongated tubular body and each configured for advancement through the distal end of the elongated tubular body; and
wherein the second lumen of the vacuum tube is concentric with the first lumen.

2. The system of claim 1, wherein the separation mechanism is selected from a group consisting of a slicing mechanism, a cutting mechanism, a weakened region of the elongated wire, and a snap-fastener mechanism.

3. The system of claim 2, wherein activation of the separation mechanism comprises the application of a proximal force.

4. The system of claim 1, wherein the snare is slidably disposed within the lumen of the tubular body adjacent to, and external of, the vacuum tube.

5. The system of claim 1, wherein the first lumen of the vacuum tube comprises a first diameter, the second lumen of the vacuum tube comprises a second diameter, and the second diameter is greater than the first diameter.

6. The system of claim 1, wherein the distal end of the snare is configured to lock in the closed position.

7. The system of claim 1, wherein the open position of the distal end of the snare is configured to receive a portion of the left atrial appendage after inversion thereof and the closed position of the distal end of the snare is configured to engage and retain at least a portion of the left atrial appendage after the inversion thereof.

8. The system of claim 1, further comprising a vacuum source coupled with the vacuum tube, the vacuum source operable to generate a vacuum within the first lumen of the vacuum tube to facilitate engagement of the target site using the distal end of the vacuum tube.

9. The system of claim 1, wherein the distal end of the vacuum tube comprises a suction flange.

10. A system for inverting an occluding a left atrial appendage, the system comprising:
a catheter configured for introduction into a mammalian blood vessel and advancement to a left atrium of a heart and into a left atrial appendage, the catheter comprising an elongated tubular body having a proximal end, a distal end, and a balloon configured for inflation and deflation, and further defining a lumen extending between the proximal and distal ends;
a vacuum tube comprising a proximal end, a distal end, a first lumen, and a second lumen extending between the proximal and distal ends, the distal end of vacuum tube configured to engage a targeted tissue;
a snare comprising an elongated wire having a proximal end, a distal end, a diameter and a separation mechanism, the snare disposed within the second lumen of the vacuum tube and outside of the first lumen of the vacuum tube, the distal end configured to move from an open position to a closed position, and the separation mechanism configured to detach the distal end from the proximal end upon activation;
an outer scaffold coupled with an exterior of the tubular body, the outer scaffold configured for expansion and to be anchored within an interior of the left atrial appendage upon expansion, the outer scaffold having a diameter, and the outer scaffold is separated from the vacuum tube; and
an occluder membrane coupled with the outer scaffold and configured to move from a constricted position to an expanded position, the expanded position of the occluder membrane configured for occluding an orifice of the left atrial appendage; and
wherein the vacuum tube and the snare are slidably disposed within the lumen of the tubular body and each configured for advancement through the distal end of the tubular body; and
wherein the second lumen of the vacuum tube is concentric with the first lumen.

11. A method for closing a left atrial appendage, the method comprising the steps of:
inverting a distal portion of a left atrial appendage; and
constraining the inverted distal portion of the left atrial appendage using a catheter system configured to fit within an interior of the left atrial appendage, the catheter system comprising:
a catheter configured for introduction into a mammalian blood vessel and advancement into the left atrial appendage, the catheter comprising an elongated tubular body having a proximal end, a distal end, and defining a lumen extending between the proximal and distal ends,
a vacuum tube comprising a proximal end, a distal end, a first lumen, and a second lumen extending between the proximal and distal ends, the distal end of vacuum tube configured to engage the distal portion of the left atrial appendage,
a snare comprising an elongated wire having a proximal end, a distal end and a separation mechanism, the snare disposed within the second lumen of the vacuum tube and outside of the first lumen of the vacuum tube, the distal end configured to move from an open position to a closed position and the separation mechanism integral with the proximal end of the elongated wire and configured to detach the distal end from the proximal end upon activation, and
wherein the vacuum tube and the snare are slidably disposed within the lumen of the elongated tubular body and each configured for advancement through the distal end of the elongated tubular body, and
wherein the second lumen of the vacuum tube is concentric with the first lumen.

12. The method of claim 11, wherein the step of constraining is performed to facilitate closure of an orifice defined by the left atrial appendage and to promote fibrosis.

13. The method of claim 11, wherein the step of constraining comprises:
introducing the distal end of the snare in the open position into the interior of the left atrial appendage;
advancing the distal end of the snare in the open position distally along the inverted distal portion of the left atrial appendage; and
moving the distal end of the snare to the closed position to engage the inverted distal portion of the left atrial appendage.

14. The method of claim 13, further comprising the step of activating the separation mechanism to detach the distal end of the snare from the proximal end of the snare.

15. The method of claim 14, wherein:
the separation mechanism is selected from a group consisting of a slicing mechanism, a cutting mechanism, a weakened region of the elongated wire, and a snap-fastener mechanism; and
the step of activating the separation mechanism comprises applying a proximal force to the snare.

16. The method of claim 13, further comprising the step of locking the distal end of the snare in the closed position.

17. The method of claim 11, wherein the vacuum tube of the system further comprises the second lumen extending between the proximal and distal ends of the vacuum tube and concentric with the first lumen and the snare is slidably disposed within the second lumen of the vacuum tube and configured for advancement through the distal end of the vacuum tube.

18. The method of claim 17, wherein:
the first lumen of the vacuum tube comprises a first diameter, the second lumen of the vacuum tube comprises a second diameter, and the second diameter is greater than the first diameter; and
the step of inverting a distal portion of a left atrial appendage comprises the steps of:
introducing the vacuum tube into the interior of the left atrial appendage,
applying suction through the vacuum tube so that the distal end of the vacuum tube engages the distal portion of the left atrial appendage, and
pulling the vacuum tube in a direction away from the distal portion of the left atrial appendage while applying suction to invert the distal portion of the left atrial appendage and reduce a diameter of the inverted distal portion of the left atrial appendage to less than the second diameter.

19. The method of claim 11, wherein:
the catheter system further comprises:
an outer scaffold coupled with an exterior of the tubular body, the outer scaffold configured for expansion and to be anchored within an interior of the left atrial appendage, and
an occluder membrane coupled to the outer scaffold and configured to move from a constricted position to an expanded position for occluding an orifice of the left atrial appendage; and the method further comprises the steps of:
introducing the outer scaffold into the interior of the left atrial appendage,
expanding the outer scaffold within the interior of the left atrial appendage to anchor the outer scaffold and initiate the expansion of the occluder membrane coupled therewith, and
occluding an orifice of the left atrial appendage with the expanded outer scaffold.

* * * * *